(12) United States Patent
Vignon et al.

(10) Patent No.: US 11,096,656 B2
(45) Date of Patent: Aug. 24, 2021

(54) INSTRUMENT ALIGNMENT AND TRACKING WITH ULTRASOUND IMAGING PLANE

(71) Applicant: KONINKLIJKE PHILIPS N.V., Eindhoven (NL)

(72) Inventors: Francois Guy Gerard Marie Vignon, Cambridge, MA (US); Ameet Kumar Jain, Cambridge, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 981 days.

(21) Appl. No.: 15/109,015

(22) PCT Filed: Jan. 2, 2015

(86) PCT No.: PCT/IB2015/050023
§ 371 (c)(1),
(2) Date: Jun. 29, 2016

(87) PCT Pub. No.: WO2015/101949
PCT Pub. Date: Jul. 9, 2015

(65) Prior Publication Data
US 2016/0324501 A1    Nov. 10, 2016

Related U.S. Application Data

(60) Provisional application No. 61/922,882, filed on Jan. 2, 2014.

(51) Int. Cl.
*A61B 8/08* (2006.01)
*A61B 8/00* (2006.01)
(Continued)

(52) U.S. Cl.
CPC .............. *A61B 8/0841* (2013.01); *A61B 8/12* (2013.01); *A61B 8/4254* (2013.01);
(Continued)

(58) Field of Classification Search
None
See application file for complete search history.

(56) References Cited

U.S. PATENT DOCUMENTS

| 4,249,539 A | 2/1981 | Vilkomerson |
| 5,158,088 A | 10/1992 | Nelson |

(Continued)

FOREIGN PATENT DOCUMENTS

| RU | 2256169 C1 | 7/2005 |
| WO | 2011138698 A1 | 11/2011 |

(Continued)

OTHER PUBLICATIONS

Spitzer, Stefan G. et al "Ablation of Typical Atrial Flutter Using a Three-Dimensional Ultrasound Mapping System", Journal of Interventional Cardiac Electrophysiology, vol. 8, pp. 181-185, 2003.
(Continued)

*Primary Examiner* — Yi-Shan Yang

(57) ABSTRACT

A tool navigation system employing an ultrasound probe, an ultrasound scanner, an interventional tool, a tool tracker and an image navigator. In operation, the ultrasound probe generates an acoustic image plane for scanning an anatomical region, and the ultrasound scanner generates an ultrasound image of the anatomical region from a scan of the anatomical region. During the scan, the interventional tool is navigated within the anatomical region relative to the acoustic image plane, and the tool tracker tracks a position of the interventional tool relative to the acoustic image plane. The image navigator displays a graphical icon within the ultrasound image for illustrating a tracking of the interventional tool relative to the acoustic image plane by the tool tracker. Additionally, a special attachment on the US probe with PZT type sensors can help this navigation by emitting acoustic waves off the central axis of the imaging plane.

15 Claims, 6 Drawing Sheets

(51) Int. Cl.
*A61B 34/20* (2016.01)
*A61B 8/12* (2006.01)
*A61B 17/34* (2006.01)
*A61B 90/00* (2016.01)

(52) U.S. Cl.
CPC ............ *A61B 8/4477* (2013.01); *A61B 8/461* (2013.01); *A61B 34/20* (2016.02); *A61B 8/4483* (2013.01); *A61B 2017/3413* (2013.01); *A61B 2034/2063* (2016.02); *A61B 2090/378* (2016.02)

(56) References Cited

U.S. PATENT DOCUMENTS

| | | | |
|---|---|---|---|
| 6,336,899 B1 | 1/2002 | Yamazaki | |
| 2009/0069679 A1* | 3/2009 | Hibi | A61B 8/0833 600/440 |
| 2009/0118612 A1* | 5/2009 | Grunwald | A61B 5/06 600/424 |
| 2010/0298704 A1 | 11/2010 | Pelissier | |
| 2010/0298705 A1* | 11/2010 | Pelissier | A61B 8/0833 600/443 |
| 2011/0245659 A1* | 10/2011 | Ma | A61B 5/066 600/424 |
| 2013/0041252 A1 | 2/2013 | Vignon | |
| 2013/0211243 A1 | 8/2013 | Zhang | |
| 2014/0152800 A1* | 6/2014 | Fomitchov | G01N 21/6458 348/79 |
| 2015/0011872 A1* | 1/2015 | Koh | A61B 5/4887 600/424 |
| 2015/0355145 A1* | 12/2015 | Peng | G01N 29/0645 73/609 |
| 2016/0038119 A1* | 2/2016 | Desjardins | A61B 17/3403 600/424 |
| 2016/0045184 A1* | 2/2016 | Courtney | A61B 8/483 600/424 |

FOREIGN PATENT DOCUMENTS

WO  WO-2011138698 A1 * 11/2011 ............ A61B 8/0841
WO  2012172458 A1    12/2012

OTHER PUBLICATIONS

Mung, Jay et al "Design and in vitro evaluation of a real-time catheter localization system using time of flight measurements from seven 3.5 MHz single element ultrasound transducers towards abdominal aortic aneurysm procedures", Ultrasonics, vol. 51, pp. 768-775, 2011.

* cited by examiner

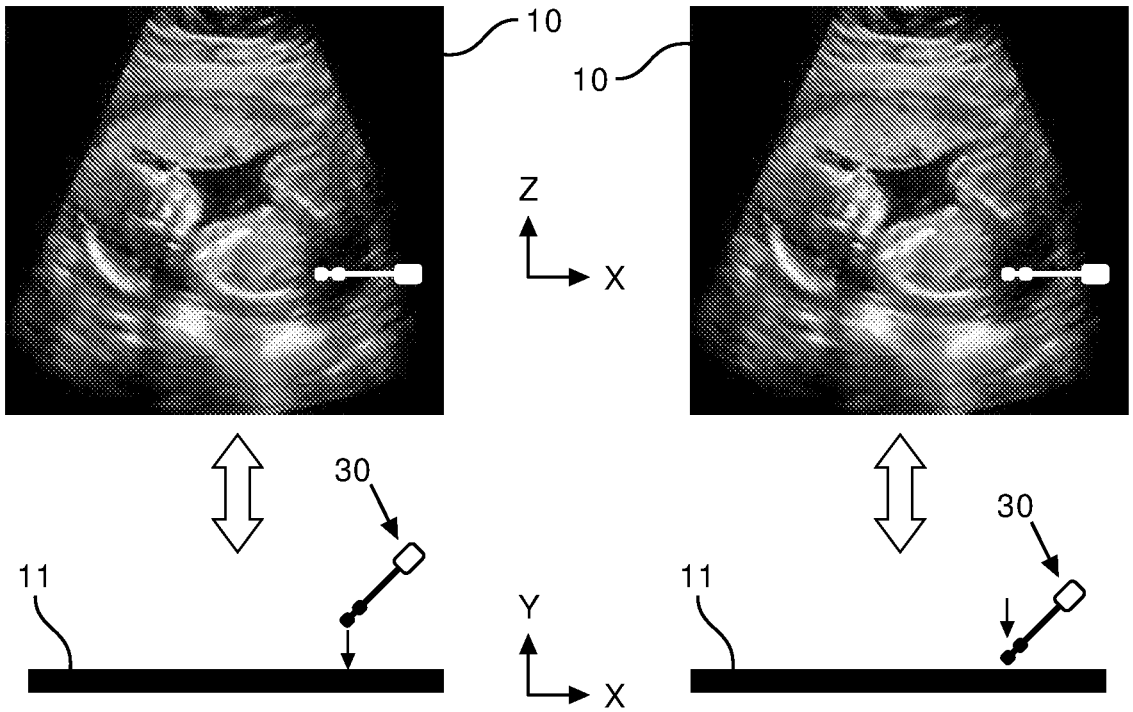
FIG. 1A
(Prior art)
FIG. 1B
(Prior art)
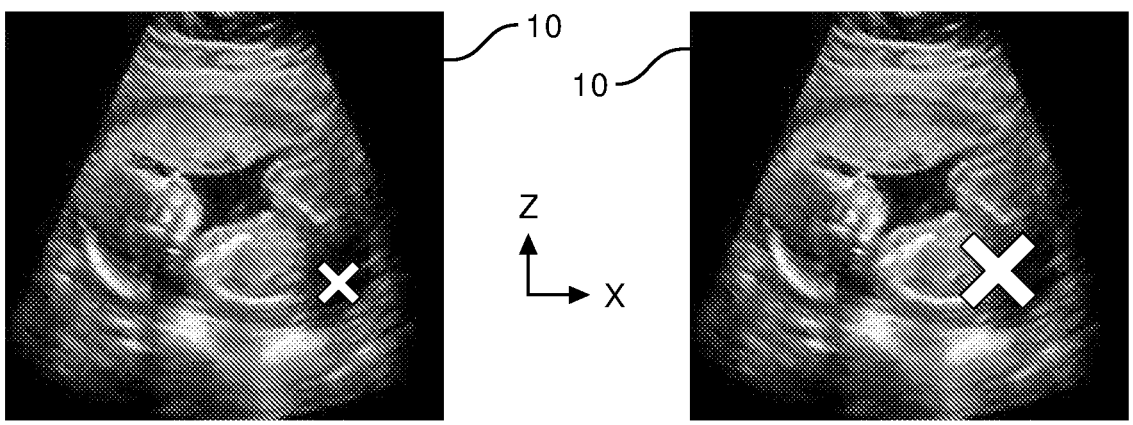
FIG. 2A
FIG. 2B

INSTRUMENT ALIGNMENT AND TRACKING WITH ULTRASOUND IMAGING PLANE

CROSS-REFERENCE TO PRIOR APPLICATIONS

This application is the U.S. National Phase application under 35 U.S.C. § 371 of International Application No. PCT/IB2015/050023, filed on Jan. 2, 2015, which claims the benefit of U.S. Provisional Patent Application No. 61/922,882, filed on Jan. 2, 2014. These applications are hereby incorporated by reference herein.

The present invention generally relates to a three-dimensional ("3D") alignment and tracking of a relative position of an interventional tool (e.g., a needle, a catheter, etc.) to an acoustic image plane generated by an acoustic imaging device (e.g., a two-dimensional ("2D") ultrasound imaging probe having a one-dimensional ("1D") transducer array). The present invention specifically relates to acoustic sensors spatially aligned relative to the interventional tool (e.g., attached to or embedded in a distal tip of a needle or a catheter) for facilitating the relative alignment and position tracking of the interventional tool to the acoustic image plane.

A 2D ultrasound probe having a 1D transducer array is commonly used for visualization of a target anatomical plane in a wide range of clinical interventions. However, it is a challenge to assess a position of an interventional tool (e.g., a needle, a catheter, etc.) outside of an acoustic imaging of the target anatomical plane generated by the 2D ultrasound probe. Consequently, a clinician may spend a lot of effort and time in trying to exactly position the interventional tool inside the acoustic image of the target anatomical plane, particularly a distal tip of the interventional tool. More particularly, for interventions involving oblique/orthogonal injection of the interventional tool into the target anatomical plane, it has proven difficult to establish an exact time and position of an entry of the interventional tool inside the acoustic image of the target anatomical plane.

For example, needle insertion under ultrasound guidance is commonly performed for various interventions (e.g., biopsies, fluid drainage, nerve blocks, vascular access, etc.). While needle visualization techniques based on steering imaging beams approximately perpendicular to the needle shaft have been implemented, in a significant number of cases the needle deviates from the acoustic image plane due to tissue heterogeneities and/or bevel asymmetry. Essentially, an out-of-plane needle disappears from the acoustic image plane irrespective of the sophistication of the smart needle visualization enhancement software. The clinician then has to move the acoustical image plane to reacquire an image of the needle, but as a result loses the acoustic image of the target anatomical plane. Furthermore, the clinician does not know where the needle is in relation to the acoustic image plane and therefore the clinician has no indication how to move the 2D ultrasound probe to find the needle.

In summary, for acoustic imaging, it is an imperative operating principle to keep imaging the target anatomical plane and at the same time know the relative position of the needle with respect to the target anatomical plane. However, one major technical difficulty for acoustic imaging is to correctly align the needle and the ultrasound imaging plane for an in-plane approach and to visualize the needle tip as opposed to the shaft for an out-of-plane approach. Small probe and needle movements lead to misalignment of the needle and image plane which in turn may result in poor needle visualization, frustration, stress, loss of time, multiple needle punctures resulting in patient discomfort, and possibly bad procedure outcomes (e.g., false-negative in biopsies, unsuccessful blocks in regional anesthesia or pain management, and vessel and nerve damage).

For example, FIGS. 1A and 1B illustrate a small Y movement of a needle 30 toward an acoustic image plane 11. This small Y movement may lead to a Y misalignment of needle 30 and acoustic image plane 11 as demonstrated by the white graphical icon identically shown in an ultrasound image 10. Additionally, needles are often poorly visualized under ultrasound, because they are specular reflectors that reflect the sound away from the imaging probe with a degree of reflection depending upon the insertion angle of the needle with in the imaging plane. Nonetheless, there is value in displaying the needle tip and expected trajectory when the needle is in plane and invisible or out of plane.

The present invention adheres to the operating principle of acoustic imaging by facilitating a tracking and visualization of the interventional tool via an overlay of a graphical icon (e.g., a marker) indicating the interventional tool on the ultrasound image. One or more features/aspects of the graphical icon (e.g., size, color, shape, etc.) is modulated as a function of a distance of the interventional tool (e.g., the tip of the interventional tool) to the ultrasound imaging plane. For example, as shown in FIGS. 2A and 2B, a size of a graphical icon illustrated as a white X marker overlain on ultrasound image 10 increases as interventional tool is moved in a Y direction of acoustic image plane 11 as shown in FIGS. 1A and 1B. This will significantly help a physician align the interventional tool with the imaging probe, which results in good confidence, fast procedures and good outcomes, particularly even when the interventional tool is invisible to conventional imaging (i.e., out of plane).

One form of the present invention is tool navigation system employing an ultrasound probe, an ultrasound scanner, an interventional tool (e.g., a needle or a catheter), a plurality of ultrasound transducers, a tool tracker and an image navigator. In operation, the ultrasound probe generates an acoustic image plane for scanning an anatomical region, and the ultrasound scanner generates an ultrasound image of the anatomical region from a scan of the anatomical region. During the scan, the interventional tool is navigated within the anatomical region relative to the acoustic image plane, and the ultrasound transducers facilitate a tracking by the tool tracker of a distance of the interventional tool relative to the acoustic image plane. The image navigator displays a graphical icon within the ultrasound image of the anatomical region as generated by the ultrasound scanner for illustrating a tracking of the interventional tool relative to the acoustic image plane by the tool tracker. One or more aspects of the graphical icon are modulated by the image navigator responsive to a distance of the interventional tool relative to the acoustic image plane as the interventional tool is navigated within the anatomical region.

The foregoing form and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

FIGS. 1A and 1B respectively illustrate exemplary views of an ultrasound images as known in the art.

FIGS. 2A and 2B respectively illustrate an exemplary modulation of a graphical icon of the present invention of the ultrasound images shown in FIGS. 1A and 1B.

Figure 3:
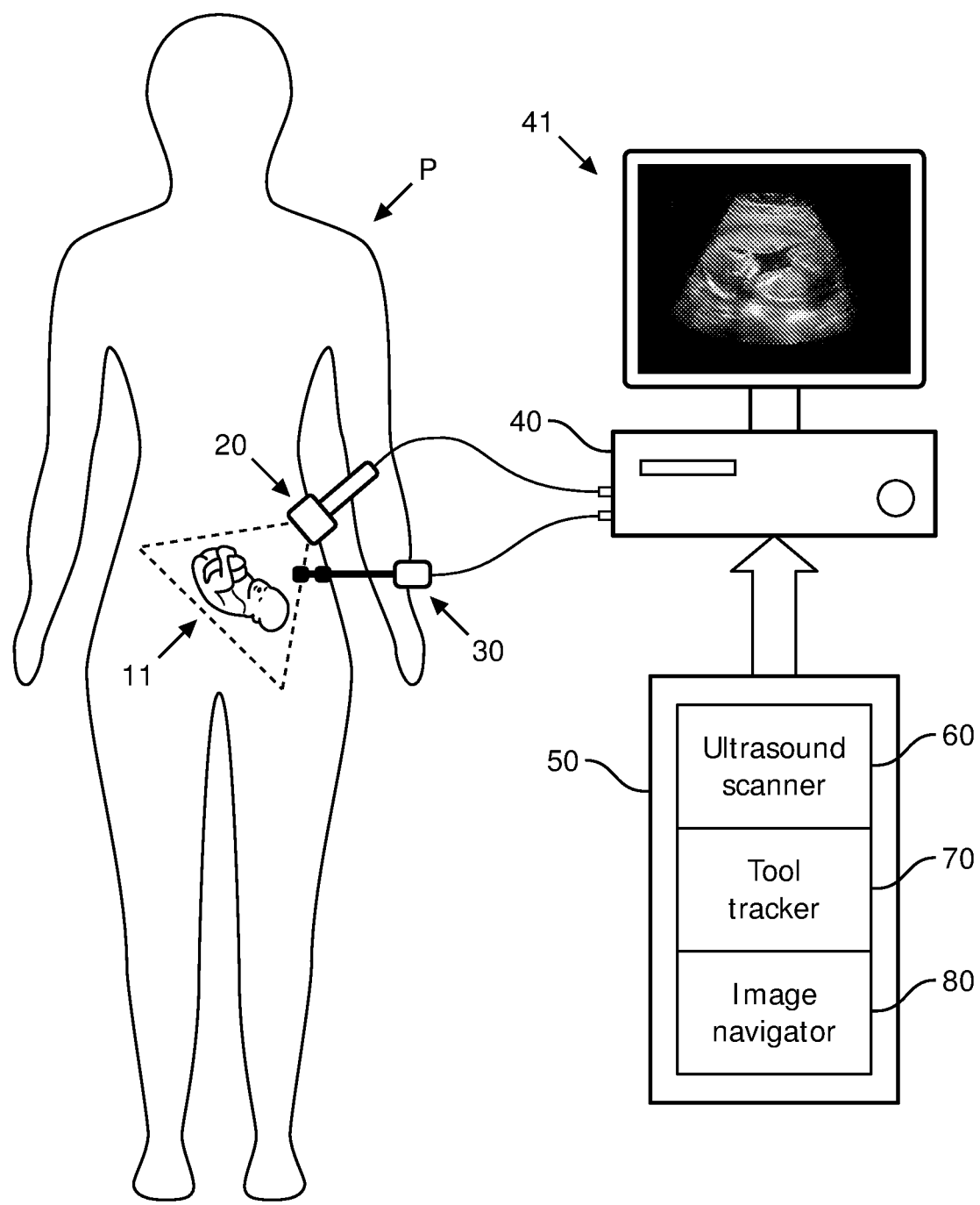
FIG. 3 illustrates an exemplary embodiment of a tool tracking system of the present invention.

To facilitate an understanding of the present invention, exemplary embodiments of the present invention will be provided herein directed to a tool navigation system shown in FIG. 3.

Referring to FIG. 3, the tool navigation system employs an ultrasound probe 20, an interventional tool 30, an ultrasound scanner 60, a tool tracker 70, and an image navigator 80.

Ultrasound probe 20 is any device as known in the art for scanning an anatomical region of a patient via acoustic energy to visualize subcutaneous body structures (e.g., tendons, muscles, joints, vessels and internal organ, etc.), such as, for example, a scanning an anatomical region 12 of a patient 11 as shown in FIG. 3. Examples of ultrasound probe 20 include, but are not limited to, a two-dimensional ("2D") ultrasound probe having a one-dimensional ("1D") transducer array, linear or curved.

Ultrasound scanner 60 is a structural configuration of hardware, software, firmware and/or circuitry as known in the art for generating an ultrasound image of the anatomical region of the patient as scanned by ultrasound probe 20 (e.g., an ultrasound image 10 of a fetus as shown in FIGS. 1-3).

Interventional tool 30 is any tool as known in the art for performing interventional procedures involving a navigation of interventional tool 30 within the anatomical region. Examples of interventional tool 30 include, but are not limited to, a needle and a catheter, and examples of interventional procedures include, but are not limited to, biopsies, fluid drainage, nerve blocks, vascular access, etc.

To facilitate the navigation in practice, interventional tool 30 may be equipped with one or more ultrasound transducers in the form of transmitters, receivers and/or transceivers as known in the art. More particularly, one ultrasound transducer provides information in a position of a designated area of interventional tool 30 (e.g., a distal tip of interventional tool 30), and two or more ultrasound transducers provide orientation information that facilitates a displaying of a projected path of interventional tool 30 and a projected intersection point with the ultrasound imaging plane 11, thus further facilitating out-of-plane approaches (which are otherwise blind).

Figure 4:
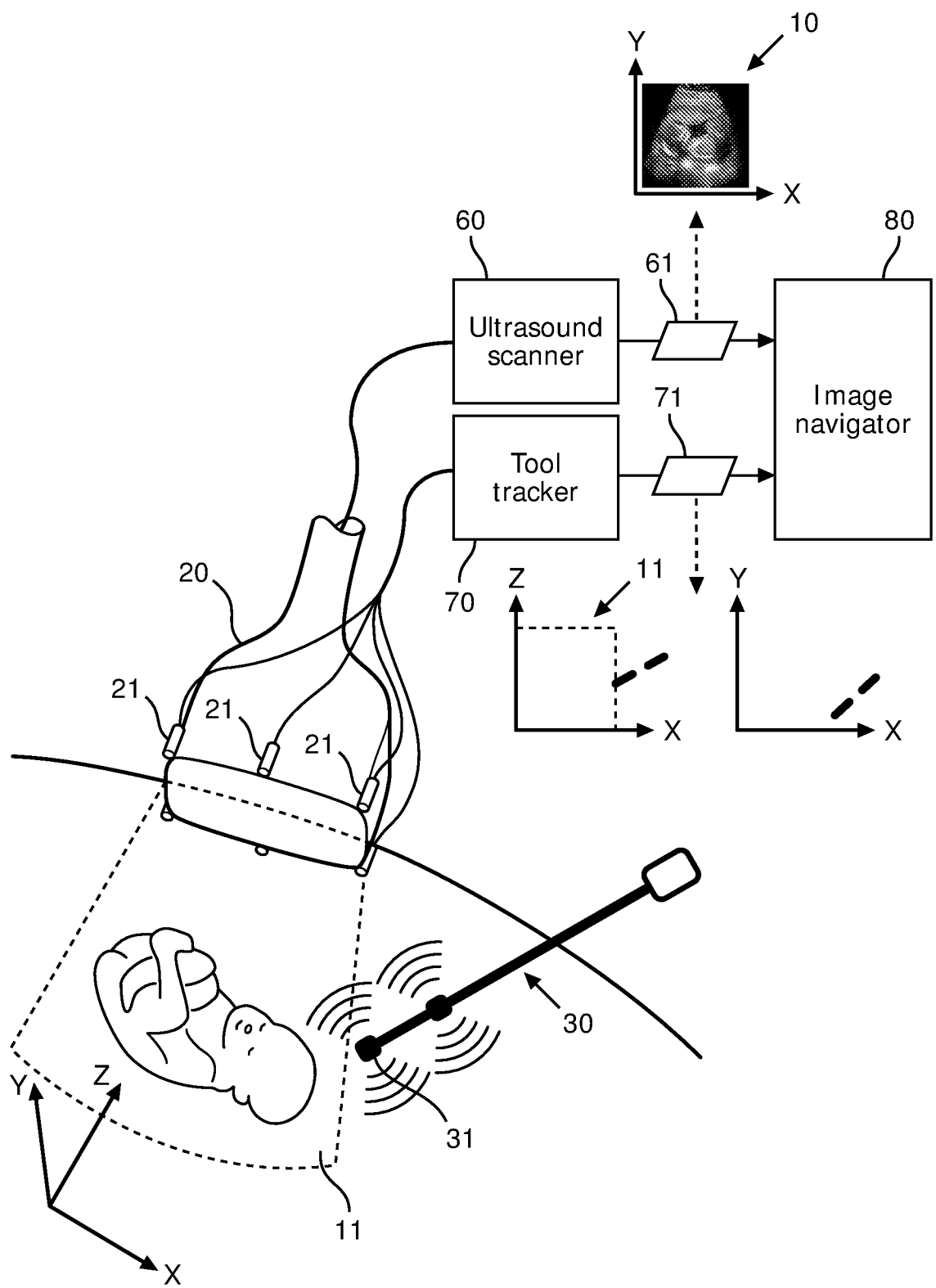
FIG. 4 illustrates an exemplary interventional procedure involving the tool tracking system shown in FIG. 3.

In one embodiment as shown in FIG. 4, a pair of ultrasound transducers 31 are embedded in a known configuration adjacent a distal tip on interventional tool 30. When operating as transmitters, ultrasound transducers 31 may either be separated by non-overlapping frequency ranges, and/or be fired one after the other to facilitate an individual tracking of ultrasound transducers 31. Similarly, when operated as receivers, signals for each ultrasound transducer 31 needs to be individualized (e.g., with non-overlapping bandwidths, a switch, two (2) independent cables, or signal processing methods for signal separation).

For this embodiment of interventional tool 30 as shown in FIG. 4, ultrasound probe 20 may be equipped with one or more ultrasound transducers 21 for tracking ultrasound transducers 31. More particularly, three (3) or more ultrasound transducers 21 yield satisfactory position estimates of ultrasound transducers 31. In practice, ultrasound transducers 21 are disposed on ultrasound probe 20 in a manner providing a wide acceptance angle in order to efficiently track ultrasound transducers 31 within a wide field of view.

In one embodiment of ultrasound probe 20 as shown in FIG. 4, six (6) ultrasound transducers 21 are disposed on a 2D surface around the array perimeter of ultrasound probe 20. In practice for this embodiment, ultrasound transducers 21 may be mounted on ultrasound probe 20 as a clip-on device or embedded in a design of ultrasound probe 20. In either case, a simple calibration between the tracked position and the image may be needed. Such a calibration may involve a clicking on tip of interventional tool 30 on a pulse-echo image under a controlled imaging environment.

Tool tracker 70 is a structural configuration of hardware, software, firmware and/or circuitry as known in the art for executing technique(s) for tracking a position of interventional tool 30 relative to the ultrasound image of the anatomical region. For the ultrasound tracking embodiment of ultrasound probe 20 and interventional tool 30 as shown in FIG. 4, tool tracker 70 executes a trilateration algorithm for determining a 3D position of ultrasound transducers 31 based on a time of flight of signals between ultrasound transducers 21 and ultrasound transducers 31.

Figure 5:
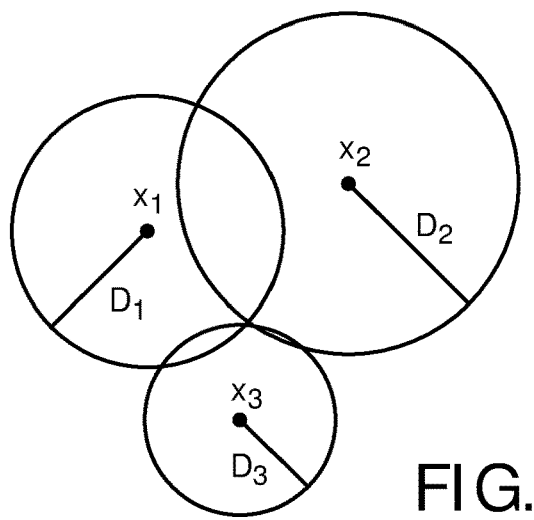
FIG. 5 illustrates an exemplary execution of a trilateration as known in the art.

In practice, three (3) pairs of location-distance are necessary to perform 3D localization and any additional pairs of location-distance increase robustness. In one embodiment, as supported by FIG. 5, a linear least-squares estimate for location of ultrasound transducers 31 may be obtained with the following equation:

$$\hat{x}_s = (S^T S)^{-1} A^T b$$

where $$S = \begin{bmatrix} x_2 \\ x_3 \\ \vdots \\ x_N \end{bmatrix}, b = \frac{1}{2} \begin{bmatrix} R_2^2 - D_2^2 + D_1^2 \\ R_3^2 - D_3^2 + D_1^2 \\ \vdots \\ R_N^2 - D_N^2 + D_1^2 \end{bmatrix},$$

$x_i = [x_i \ y_i \ z_i]$ denotes a location of an $i^{th} = 1, \ldots, N$) transducers 21, $R_i = \|x_i\|$ is a distance from virtual transducer 21 to a coordinate frame origin, $D_i = \|x_i - x_s\|$ is a distance between each transducer 21 and sensor 31, and $x_1 = [0 \ 0 \ 0]$ is the location of each transducer 21 designated as the origin.

In an alternative embodiment utilizing ultrasound transducers 31 and omitting ultrasound transducers 21, tool tracker 70 executes an algorithm for computing sensor position with respect to the imaging frame of reference. More particularly, tool tracker 70 determines a projection of a 3D position (X-azimuth, Z-depth, Y-elevation) onto a 2D position in the imaging plane 12 (x-z or r-theta). For this embodiment, a Z-depth (or range) coordinate is obtained by measuring a time of flight of ultrasound signals from ultrasound probe 20 to ultrasound transducers 31, and an X-azimuth (or angular) position is obtained by searching for a maximum received amplitude across received beams at ultrasound transducers 31. A qualitative estimate of the Y coordinate (distance of the sensors 31 to imaging plane 11) is obtained by recording the received amplitude of the signals at transducers 31 and comparing it to a past history: increasing amplitude generally means that the sensors 31 are approaching imaging plane 11, whereas a decreasing amplitude means that the sensors 31 are going further away from imaging plane 11.

Image navigator 80 is a structural configuration of hardware, software, firmware and/or circuitry as known in the art for executing technique(s) for displaying an ultrasound image as generated by ultrasound scanner 60 and in accordance with the present invention for generating a graphical icon for illustrating a tracking of interventional tool 30 relative to the acoustic image plane 11 by tool tracker 70. More particularly, as interventional tool 30 is navigated within the anatomical region, image navigator 80 modulates one or more aspects of the graphical icon (e.g., size, color, shape) to qualitatively indicate a tracked distance of the interventional tool 30 relative to the acoustic image plane 11. To this end, image navigator 80 inputs data 61 from ultrasound scanner 60 representative of ultrasound image 10 and inputs data 71 from tool tracker 70 representative of a 3D position (X-azimuth, Z-depth) of interventional tool 30 relative to acoustic image plane 11.

Figure 6:
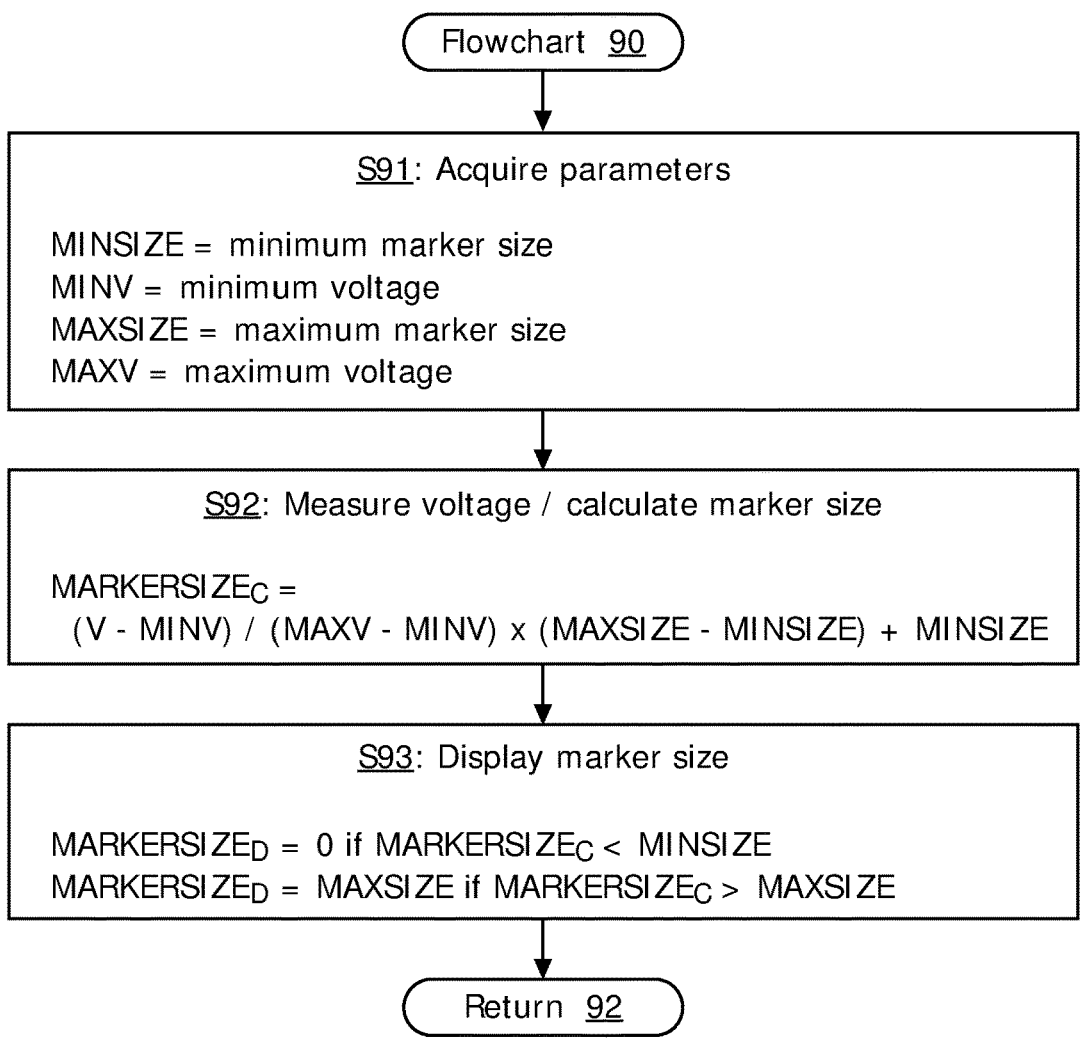
FIG. 6 illustrates a flowchart representative of a first exemplary embodiment of a graphical icon modulation method in accordance with the present invention.
Figure 7:
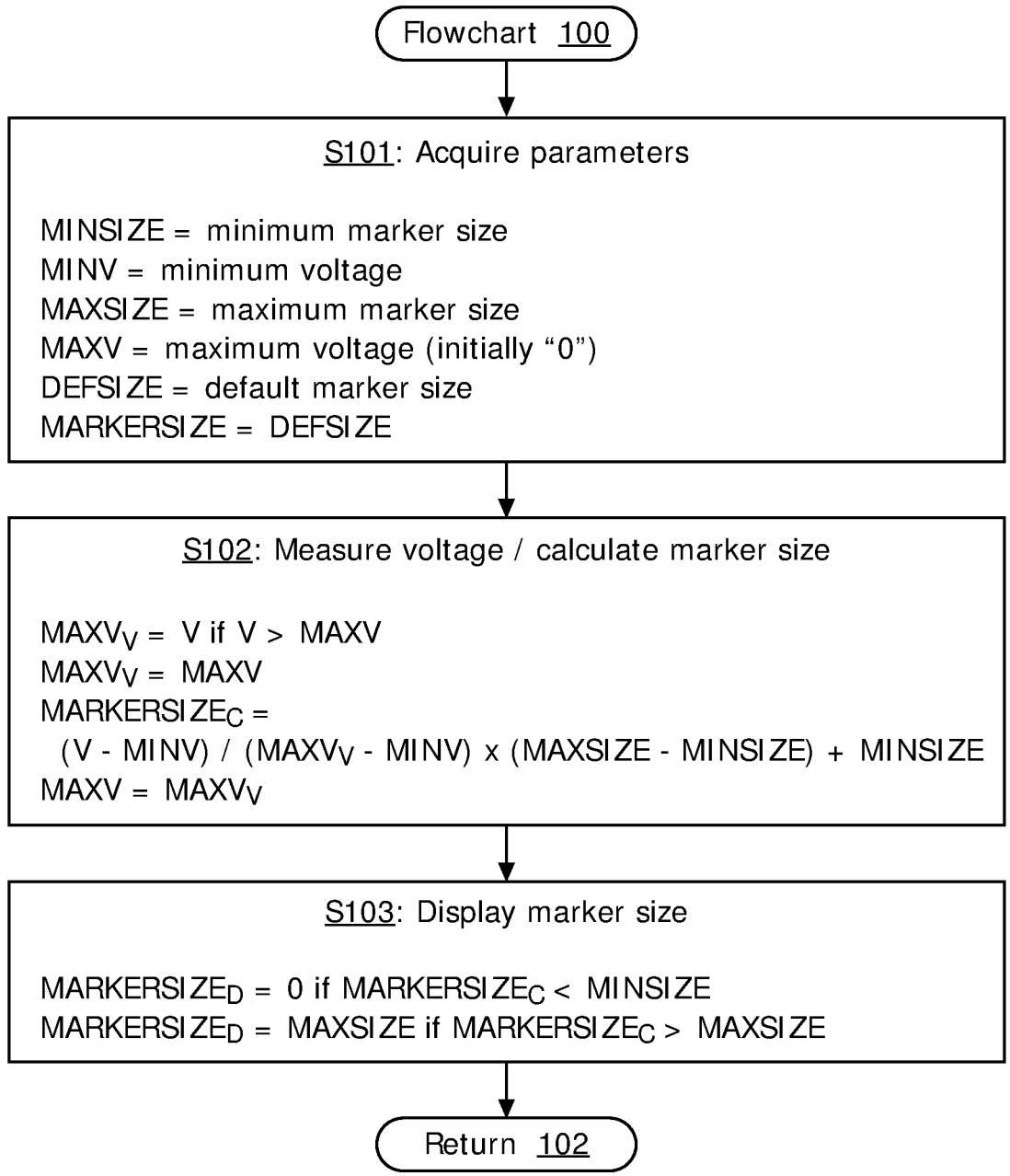
FIG. 7 illustrates a flowchart representative of a second exemplary embodiment of a graphical icon modulation method in accordance with the present invention.
Figure 8:
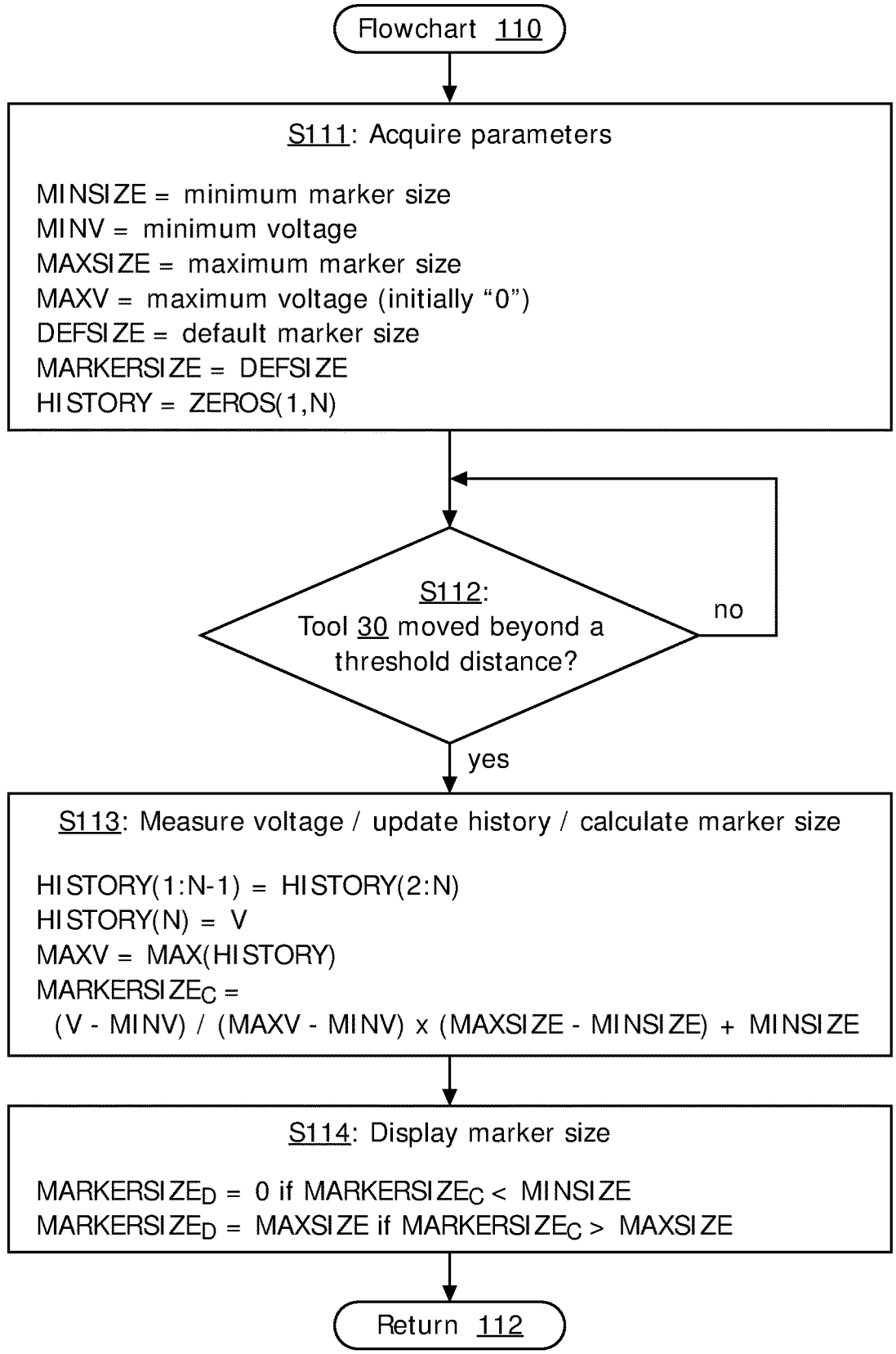
FIG. 8 illustrates a flowchart representative of a third exemplary embodiment of a graphical icon modulation method in accordance with the present invention.

To facilitate an understanding of the graphical icon modulation, exemplary embodiments of image navigator 80 will be provided herein directed to a size modulation of a marker as shown in FIGS. 6-8 to qualitatively indicate a distance of the ultrasound transducers 31 to ultrasound image plane 11. While these exemplary embodiments uses the amplitudes or signal-to-noise ratios SNRs of received signals and compares them to a history of received amplitudes or SNRs to modulate the marker appearance, those having ordinary skill in the art will appreciate how to apply the principles of these exemplary embodiments to other modulated aspects (e.g., shape, color, bar graph, etc.) and signals quantifying of the Y-elevation distance. Those having ordinary skill in the art will also appreciate various modifications and variations of these exemplary embodiments of graphical icon modulation.

Generally, it is desired that the size of the marker (the variable 'markerSize') is maximum (to a fixed maximum size 'maxSize') when the signal level (V) at ultrasound transducer 31 drops below a certain voltage or a certain SNR, and minimum (to a fixed minimum size 'minSize') when an ultrasound transducer 31 is on imaging plane 11 at any depth. At intermediate levels, the size of the marker is intermediate. In practice, the size of the marker may be the size of the marker (the variable 'markerSize') is maximum (to a fixed maximum size 'maxSize') when an ultrasound transducer 31 is on imaging plane 11 at any depth, and minimum (to a fixed minimum size 'minSize') when the signal level (V) at ultrasound transducer 31 drops below a certain voltage or a certain SNR.

Also in practice, a curve markerSize=f(V) or markerSize=f(SNR) should be monotonically increasing or decreasing, but may be linear as described herein or non-linear (e.g. logarithmic). When the signal levels drop below the set minimum acceptable signal level (minV or minSNR), the marker is not displayed on the screen. In all embodiments as shown in FIGS. 6-8, the minimum marker size ('minSize') corresponds to the minimum acceptable received voltage or received SNR, which is a fixed parameter ('minV'/'minSNR'). At lower received signal levels, the marker is no longer displayed. This eliminates the possibility to display potentially wrong sensor locations in low-SNR scenarios.

In a fixed max voltage embodiment, from the minimum marker size 'minSize', a monotonically increasing curve of size versus received signal amplitude or SNR is implemented. The marker size "markerSize" is thus directly representing the received signal strength, which increases at a given depth as ultrasound transducer 31 approaches the imaging plane 11 and decreases as it goes away from the imaging plane 11. In order to limit the maximum size of the marker, it may be decided that the marker stops to grow beyond 'max Size' after a maximum acceptable signal strength 'maxV'.

FIG. 6 illustrates a flowchart 90 representative of an exemplary fixed max voltage embodiment. Referring to FIG. 6, a stage S91 of flowchart 90 encompasses image navigator 80 acquiring parameters necessary for a calculation by image navigator 80 of 'markerSize$_C$' during a stage S92 of flowchart 90 as a function of the measured voltage V indicative of the received signal amplitude in accordance with the following equation:

$$\text{markerSize}_C = (V - \text{min}V)/(\text{max}V - \text{min}V) * (\text{maxSize} - \text{minSize}) + \text{minSize}$$

A stage S93 of flowchart 90 encompasses image navigator 80 displaying a 'markerSize$_D$' in accordance with the following equations:

$$\text{markerSize}_D = 0 \text{ if markerSize}_C < \text{minsize}$$

$$\text{markerSize}_D = \text{maxSize if markerSize}_C > \text{maxSize}$$

Image navigator 80 returns to stage S92 to repeat stages S92 and S93 as needed.

In a variable max voltage embodiment, the maximum marker size ('maxSize') is variable and corresponds to the maximum signal strength received by ultrasound transducer 31 since the experiment was started (variable 'maxV'). Each time a signal is received, its strength is compared to the maximum past received signal. If it exceeds it, the signal 'maxV' corresponding to the maximum marker size is updated. This embodiment ensures a maximum marker size excursion as interventional tool 30 is advanced within the anatomical region.

FIG. 7 illustrates a flowchart 100 representative of an exemplary variable max voltage embodiment. Referring to FIG. 7, a stage S101 of flowchart 100 encompasses image navigator 80 acquiring parameters necessary for a calculation by image navigator 80 of 'markerSize$_C$' during a stage S102 of flowchart 100 as a function of the measured voltage V indicative of the received signal amplitude compared to variable 'maxV$_V$'. Specifically, an initial implementation of stage S101 involves setting 'maxV' to 0 and markerSize to a 'defaultSize', and stage S102 involves a setting of 'maxV$_V$' to the measured voltage V if measured voltage V is greater than 'maxV' or otherwise setting 'maxV$_V$'='maxV'. The setting of 'maxV$_V$' is inputted to the calculation of 'markerSize$_C$' in accordance with the following equation:

$$\text{markerSize}_C = (V - \text{min}V)/(\text{max}V_V - \text{min}V) * (\text{maxSize} - \text{minSize}) + \text{minSize}$$

Thereafter, 'maxV'='maxV$_V$'.

A stage S93 of flowchart 90 encompasses image navigator 80 displaying a 'markerSize$_D$' in accordance with the following equations:

$$\text{markerSize}_D = 0 \text{ if markerSize}_C < \text{minsize}$$

$$\text{markerSize}_D = \text{maxSize if markerSize}_C > \text{maxSize}$$

Image navigator 80 returns to stage S102 to repeat stages S102 and S103 as needed.

The fixed max voltage and the variable max voltage embodiments ensure displaying a growing marker as ultrasound transducer 31 is moved toward the imaging plane 11 at a given imaging depth. However, as known in the art, the received signal amplitude also depends on depth so that the variation of marker size as a function of out-of-plane distance is depth-dependent, and changes in sensor depth also will result in changes in marker size.

In order to mitigate or eliminate this effect, in a minimal movement embodiment, the current received signal amplitude is compared to a short history of signal amplitudes. The history length is a set parameter typically set to a few seconds of data, or a characteristic time for sensor advancement into the ultrasound field. The maximum marker size (a set parameter) is set to correspond to the maximum received signal or SNR during this history. As a further refinement, the history file is updated each time ultrasound transducer 31 is measured to move significantly (over a set distance threshold) as measured by its tracked position. This guarantees that the maximum set marker size will be displayed when ultrasound transducer 31 is in plane at any depth, provided that the characteristic time of cross-plane motion is faster than that of depth motion.

FIG. 8 illustrates a flowchart 110 representative of the minimal movement embodiment. Referring to FIG. 8, a stage S111 of flowchart 110 encompasses image navigator 80 acquiring parameters necessary for a calculation by image navigator 80 of 'markerSize$_C$' during a stage S113 of flowchart 110 as a function of a history of measured voltage V indicative of the received signal amplitude as related to movement of interventional tool 30. Specifically, an initial implementation of stage S111 involves setting 'maxV' to 0; markerSize to a 'defaultSize', and a history to zeros.

A stage S112 of flowchart 110 encompasses image navigator 80 determining whether interventional tool 30 has been moved beyond a threshold distance. If so, image navigator 80 proceeds to stage S113 to update the history with measured voltage V in accordance with the following equations:

history(1:$N$−1)=history(2:$N$)

history($N$)=$V$ max$V$=max(history)

markerSize$_C$=($V$−min$V$)/(max$V$−min$V$)*(maxSize−minSize)+minSize

A stage S113 of flowchart 110 encompasses image navigator 80 displaying a 'markerSize$_D$' in accordance with the following equations:

markerSize$_D$=0 if markerSize$_C$<minsize markerSize$_D$=maxSize if markerSize$_C$>maxSize Image navigator 80 returns to stage S112 to repeat stages S112-S114 as needed.

All the above embodiments may advantageously modified by taking into account the measured current spatial position, especially the depth, of interventional tool 30. Specifically, as known in the art, a field amplitude varies with depth and out-of-plane distance (and to a lesser extent with azimuth). The goal is to eliminate the variation in displayed marker size as a function of depth, but keep the variations on marker size as a function of out-of-plane distance at a given depth.

The following is a discussion on various possible schemes to incorporate depth (and azimuth) information in the display flowcharts of FIGS. 6-8.

First for the fixed maximum voltage embodiment of FIG. 6, instead of a fixed maximum marker size (variable 'maxSize'), a look-up table of marker sizes as a function of depth (and possibly azimuth or azimuth angle as well) is established. This table is built based on some calibration of the spatial field which is achieved beforehand by simulation or/and measurement or on-the-fly by simulation. Different look-up tables may be used for different probes, imaging modes, settings (e.g. beam density) and transmit focal depth, for varying degrees of accuracy. The bulk attenuation within the anatomical region may be measured by fitting an exponential to the curve giving backscattered data amplitude as a function of depth (on the pulse-echo data), and added as an input to the simulation. Further, the maximum marker size may be a function of interventional tool 30.

Second, in embodiments setting maxV as the maximum past read value in a history file, the current read voltage is compared only to those voltage readings in the history with a similar depth (e.g., no further than 1 cm away from the current reading).

Third, a coarse spatial grid may be established and for each pixel in that grid, the maximum read value in the corresponding area is set as the local maximum read value maxV. These latter embodiments may be with the field simulation by constraining the simulation with actual readings.

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. A tool navigation system, comprising:
  an ultrasound probe configured to generate an acoustic image plane for scanning an anatomical region;
  an ultrasound scanner operatively connected to the ultrasound probe, the ultrasound scanner being configured to generate an ultrasound image of the anatomical region;
  an interventional tool configured to be insertable and navigated within the anatomical region relative to the acoustic image plane, said interventional tool having a distal tip;
  at least one ultrasound transducer connected to the interventional tool and insertable with the interventional tool within the anatomical region, said at least one ultrasound transducer being disposed on the distal tip of the interventional tool;
  wherein at least one ultrasound tracking signal is communicated between the ultrasound probe and the at least one ultrasound transducer of the interventional tool, said at least one ultrasound tracking signal being indicative of a distance of the interventional tool relative to the acoustic image plane as the interventional tool is navigated within the anatomical region;

a tool tracker operatively connected to the at least one ultrasound transducer to track the distance of the interventional tool relative to the acoustic image plane, said tool tracker being configured to estimate the distance of the interventional tool relative to the acoustic image plane as a function of the at least one ultrasound tracking signal; and an image navigator operatively connected to the ultrasound scanner and the tool tracker to display a graphical icon on the ultrasound image of the anatomical region as generated by the ultrasound scanner for illustrating a tracking by the tool tracker of the distance of the interventional tool relative to the acoustic image plane, wherein the image navigator is configured to modulate at least one aspect of the graphical icon responsive to the distance of the interventional tool relative to the acoustic image plane as tracked by the tool tracker; and wherein the image navigator is configured to monotonically modulate the at least one aspect of the graphical icon as a function of at least one of an amplitude and a signal-to-noise ratio of the at least one ultrasound tracking signal received at the at least one ultrasound transducer.

2. The tool navigation system of claim 1, wherein the tool tracker is further configured to measure a time of flight of the at least one ultrasound tracking signal between the ultrasound probe and the interventional tool.

3. The tool navigation system of claim 2, wherein the tool tracker is further configured to determine a position of the at least one ultrasound transducer connected to the interventional tool within the anatomical region relative to the acoustic image plane as a function of the time of flight of the at least one ultrasound tracking signal between the ultrasound probe and the interventional tool.

4. The tool navigation system of claim 1, wherein the image navigator is further configured to monotonically modulate the at least one aspect of the graphical icon between a fixed minimum amplitude and a fixed maximum amplitude of the at least one ultrasound tracking signal.

5. The tool navigation system of claim 1, wherein the image navigator is further configured to monotonically modulate the at least one aspect of the graphical icon between a fixed minimum signal-to-noise ratio and a fixed maximum signal-to-noise ratio of the at least one ultrasound tracking signal.

6. The tool navigation system of claim 1, wherein the image navigator is further configured to monotonically modulate the at least one aspect of the graphical icon between a fixed minimum signal-to-noise ratio and a variable maximum signal-to-noise ratio of the at least one ultrasound tracking signal, the variable maximum signal-to-noise ratio being variable based on properties of the at least one ultrasound tracking signal.

7. The tool navigation system of claim 1, wherein the image navigator is further configured to monotonically modulate the at least one aspect responsive to a minimal movement of the interventional tool perpendicular to the acoustic image plane as tracked by the tool tracker, said minimal movement being movement of the interventional tool perpendicular to the acoustic image plane less than a predetermined threshold distance.

8. The tool navigation system of claim 1, wherein the at least one aspect of the graphical icon includes at least one of a size, a shape and a color of the graphical icon.

9. The tool navigation system of claim 1, wherein the tool tracker is further configured to determine a position of the at least one ultrasound transducer connected to the interventional tool within the anatomical region relative to the acoustic image plane as a function as a function of a maximum received amplitude across beams from the ultrasound probe received at the at least one further ultrasound transducer.

10. The tool navigation system of claim 1, wherein the tool tracker is further configured to determine a position of the at least one ultrasound transducer connected to the interventional tool within the anatomical region relative to the acoustic image plane as a function of an amplitude of the at least one ultrasound tracking signal received by the at least one ultrasound transducer.

11. A tool navigation system, comprising:
an ultrasound probe, including a transducer array, operable to generate an acoustic image plane for scanning an anatomical region, the ultrasound probe having a plurality of ultrasound transducers forming the transducer array;

an ultrasound scanner operatively connected to the ultrasound probe, the ultrasound scanner configured to generate an ultrasound image of the anatomical region;

an interventional tool operable to the navigated within the anatomical region relative to the acoustic image plane, the interventional tool including at least one further ultrasound transducer insertable with the interventional tool into the anatomical region, wherein the plurality of ultrasound transducers of the ultrasound probe and the at least one further ultrasound transducer of the interventional tool communicate at least one ultrasound tracking signal indicative of a distance of the interventional tool relative to the acoustic image plane as the interventional tool and the at least one further ultrasound transducer are navigated within the anatomical region;

a tool tracker operatively connected to the plurality of ultrasound transducers to track the distance of the interventional tool relative to the acoustic image plane, wherein said tool tracker is configured to determine the distance of the interventional tool relative to the acoustic image plane as a function of a maximum received amplitude across beams from the ultrasound probe received at the at least one further ultrasound transducer; and an image navigator operatively connected to the ultrasound scanner and the tool tracker to display a graphical icon on the ultrasound image of the anatomical region as generated by the ultrasound scanner for illustrating a tracking by the tool tracker of the distance of the interventional tool relative to the acoustic image plane as tracked by the tool tracker.

12. The tool navigation system of claim 11, wherein the image navigator is operable to modulate at least one of a size, a shape and a color of the graphical icon responsive to the distance of the interventional tool relative to the acoustic image plane as tracked by the tool tracker.

13. The tool navigation system of claim 11, wherein the image navigator is configured to monotonically modulate the at least one aspect of the graphical icon as a function of at least one of an amplitude and a signal-to-noise ratio of the at least one ultrasound tracking signal.

14. The tool navigation system of claim 11, wherein the tool tracker is further configured to determine a position of the at least one further ultrasound transducer connected to the interventional tool within the anatomical region relative to the acoustic image plane as a function of at time of flight of the at least one ultrasound tracking signal between the plurality of ultrasound transducers and the at least one further ultrasound transducer.

15. The tool navigation system of claim 11, wherein the tool tracker is further configured to determine a position of the at least one further ultrasound transducer connected to the interventional tool within the anatomical region relative to the acoustic image plane as a function of an amplitude of the at least one ultrasound tracking signal received by the at least one further ultrasound transducer.

* * * * *